US008268797B2

(12) United States Patent
Graff

(10) Patent No.: US 8,268,797 B2
(45) Date of Patent: Sep. 18, 2012

(54) COMBINATION THERAPY FOR THE TREATMENT OF CANCER

(75) Inventor: Jeremy Richard Graff, Indianapolis, IN (US)

(73) Assignee: Isis Pharmaceuticals, Inc., Carlsbad (CA)

( * ) Notice: Subject to any disclaimer, the term of this patent is extended or adjusted under 35 U.S.C. 154(b) by 0 days.

(21) Appl. No.: 13/130,038

(22) PCT Filed: Nov. 17, 2009

(86) PCT No.: PCT/US2009/064666
§ 371 (c)(1),
(2), (4) Date: Aug. 2, 2011

(87) PCT Pub. No.: WO2010/059575
PCT Pub. Date: May 27, 2010

(65) Prior Publication Data
US 2011/0280963 A1 Nov. 17, 2011

Related U.S. Application Data

(60) Provisional application No. 61/116,910, filed on Nov. 21, 2008.

(51) Int. Cl.
*A61K 48/00* (2006.01)
*C07H 21/04* (2006.01)
*C07H 21/02* (2006.01)

(52) U.S. Cl. ... 514/44; 536/23.1; 536/24.31; 536/24.33; 536/24.5

(58) Field of Classification Search .................. None
See application file for complete search history.

(56) References Cited

U.S. PATENT DOCUMENTS

| 5,801,154 | A | 9/1998 | Baracchini et al. |
| 6,582,908 | B2 | 6/2003 | Fodor et al. |
| 2001/0053519 | A1 | 12/2001 | Fodor et al. |
| 2003/0228597 | A1 | 12/2003 | Cowsert et al. |
| 2007/0031844 | A1 | 2/2007 | Khvorova et al. |

FOREIGN PATENT DOCUMENTS

| WO | WO 01/96388 | 12/2001 |
| WO | WO 02/10409 | 2/2002 |
| WO | WO 02/44321 | 6/2002 |
| WO | WO 2004/113496 | 12/2004 |
| WO | WO 2005/028628 | 3/2005 |

OTHER PUBLICATIONS

Altmann et al., "Novel Chemistry" Applied Antisense Oligonucleotide Technology (Stein & Krieg, Eds.), pp. 73-107, Wiley-Liss: New York (1998).
Barnhart et al., "Taking aim at translation for tumor therapy" The Journal of Clinical Investigation (2007) 117(9):2385-2388.
Blagoaklonny et al., "Oligonucleotides protect cells from the cytotoxicity of several anti-cancer chemotherapeutic drugs" Anticancer Drugs (1994) 5(4):437-442.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Cleator et al., "Gene expression patterns for doxorubicin (Adriamycin) and cyclophosphamide (Cytoxan) (AC) response and resistance" Breast Cancer Research and Treatment (2006) 95(3):229-233.
Crooke et al., "Basic Principles of Antisense Therapeutics" Antisense Research and Application (1998) Chapter 1:1-50.
Crooke, "Progress in Antisense Technology" Annual Review of Medicine: Selected Topics in the Clinical Sciences (2004) 55:61-95.
De Benedetti et al., "eIF4E expression in tumors: its possible role in progression of malignancies" Intl. Journal of Biochemistry and Cell Biology (1999) 31(1):59-72.
De Benedetti et al., "Expression of antisense RNA against Initiation Factor eIF-4E mRNA in HeLa Cells Results in Lengthened Cell Division Times, Diminished Translation Rates, and Reduced Levels of both eIF-4E and the p220 Component of eIF-4F" Molecular and Cellular Biology (1991) 11(11):5435-5445.
De Benedetti et al., "Expression of Antisense RNA against eIF-4E mRNA in HeLa Cells Results in Diminished Translation Rates, Lengthened Doubling Time, and a Requirement for eIF-4F in vitro" FASEB Journal, 75th Annual Meeting, Atlanta, GA, Apr. 21-25, 1991 Abstracts Part III, Abstract 6760:A1536(1991).
De Benedetti et al., "eIF-4E expression and its role in malignancies and metastases" Oncogene (2004) 23:3189-3199.
Dong et al., "Tumor-specific RNAi targeting eIF4E suppresses tumor growth, induces apoptosis and enhances cisplatin cytotoxicity in human breast carcinoma cells" Breast Cancer Research and Treatment (2008) 113(3):443-456.
Graff et al., "The Protein Kinase Cβ-Selective Inhibitor, Enzastaurin (LY317615.HCI), Suppresses Signaling through the AKT Pathway, Induces Apoptosis, and Suppresses Growth of Human Colon Cancer and Glioblastoma Xenografts" Cancer Res. (2005) 65:7462-7469.
Graff et al., "Therapeutic suppression of translation initiation factor eIF4E expression reduces tumor growth without toxicity" The Journal of Clinical Investigation (2007) 117(9):2638-2648.
Groothuis, "The blood-brain and blood-tumor barriers: A review of strategies for increasing drug delivery" Neuro-Oncology (2000) 2(1):45-59.

(Continued)

*Primary Examiner* — Amy Bowman
(74) *Attorney, Agent, or Firm* — Isis Pharmaceuticals, Inc Patent Dept; Jones Day

(57) ABSTRACT

The present invention provides methods of sensitizing lung cancer cells to cisplatin and inhibiting the growth of lung cancer tumors by employing a modified eIF-4E antisense oligonucleotide and cisplatin in combination.

12 Claims, No Drawings

OTHER PUBLICATIONS

Jaramillo et al., "Multiple mRNAs Encode the Murine Translation Initiation Factor eIF-4E" The Journal of Biological Chemistry (1991) 266(16):10446-10451.

Jen et al., "Suppression of Gene Expression by Targeted Disruption of Messenger RNA: Available Options and Current Strategies" Stem Cells (2000) 18:307-319.

Khoury, "Eukaryotic initiation factor-4E (eIF-4E) and cyclin D1 expressions are associated with patient survival in lung cancer: A study utilizing high-density tissue microarray and immunohistochemistry" Proc Amer Assoc Cancer Res (2005) 46:1279, Abstract #5419.

Lee et al., "Akt1 inhibition by RNA interference sensitizes human non-small cell lung cancer cells to cisplatin" International Journal of Cancer (2008) 122(10):2380-2384.

Mahato et al., "Modulation of gene expression by antisense and antigene oligodeoxynucleotides and small interfering RNA" Expert Opinion on Drug Delivery (2005) 2(1):3-28.

Marra et al., "Anticancer drugs and hyperthermia enhance cytotoxicity induced by polyamine enzymatic oxidation products" Amino Acids; The Forum for Amino Acid and Protein Research (2007) 33(2):273-281.

Matzura et al., "RNAdraw; an integrated program for RNA secondary structure calculation and analysis under 32-bit Microsoft Windows" Computer Applications in the Biosciences (1996) 12(3):247-249.

Meric et al., "Translation Initiation in Cancer: A Novel Target for Therapy" Molecular Cancer Therapeutics (2002) 1:971-979.

Metro et al., "Taxanes and Gemcitabine Doublets in the Management of HER-2 Negative Metastatic Breast Cancer: Towards Optimization of Association and Schedule" Anticancer Res. (2008) 2(2B):1245-1258.

Mizushima et al., "Reduction of cisplatin cytotoxicity on human lung cancer cell lines with N-myc amplification by pretreatment with N-myc antisense oligodeoxynucleotides." Anticancer Res. (1995) 15(1):37-43.

New England Biolabs 1998/99 Catalog (cover page and pp. 121 and 284).

Olie et al., "A Novel Antisense Oligonucleotide Targeting Survivin Expression Induces Apoptosis and Sensitizes Lung Cancer Cells to Chemotherapy" Cancer Research (2000) 60:2805-2809.

Oridate et al., "Growth inhibition of head and neck squamous carcinoma cells by small interfering RNAs targeting eIF4E or cyclin D1 alone or combined with cisplatin" Cancer Biology and Therapy (2005) 4(3):318-323.

Reynolds et al., "Rational siRNA design for RNA interference" Nature Biotechnology (2004) 22(3):326-330.

Rychlik et al., "Amino acid sequence of the mRNA cap-binding protein from human tissue" PNAS (1987) 84:945-949.

Sanghvi et al., "Heterocyclic Base Modifications in Nucleic Acids and Their Applications in Antisense Oligonucleotides" Antisense Research and Applications (1993) pp. 273-288.

Scherer et al., "Approaches for the sequence-specific knockdown of mRNA" Nature Biotechnology (2003) 21(120:1457-1465.

Seki et al., "Expression of eukaryotic initiation factor 4E in atypical adenomatous hyperplasia and adenocarcinoma of the human peripheral lung" Clinical Cancer Research (2002) 8(10):3046-3053.

Stinchcombe et al., "Considerations for Second-Line Therapy of Non-Small Cell Lung Cancer" Oncologist (2008) 13, Suppl. 1):28-36.

Vickers et al., "Efficient Reduction of Target RNAs by Small Interfering RNA and Rnase H-dependent Antisense Agents" Journal of Biological Chemistry (2003) 278(9):7108-7118.

Wang et al., "Molecular Basis of Cellular Response to Cisplatin Chemotherapy in Non-Small Cell Lung Cancer (Review)" Oncology Reports (2004) 12(5):955-965.

Yamagiwa et al., "Translational regulation by p38 mitogen-activated protein kinase signaling during human cholangiocarcinoma growth" Hepatology (2003) 38(1):158-166.

Yang et al., "Contribution of eIF-4E inhibition to the expression and activity of heparanase in human colon adenocarcinoma cell line: LS-174T" World J. Gastroenterol. (2003) 9(8):1707-1712.

Zimmer et al., "Translation Control of Malignancy: the mRNA cap-Binding Protein, eIF-4E, as a Central Regulator of Tumor Formation, Growth, Invasion and Metastasis" Anticancer Research (2000) 20:1343-1352.

International Search Report for application PCT/US2004/030436 dated May 11, 2005.

International Search Report for application PCT/US2009/064666 dated Aug. 6, 2010.

International Search Report for application PCT/US2009/064649 dated Mar. 24, 2010.

COMBINATION THERAPY FOR THE TREATMENT OF CANCER

CROSS REFERENCED TO RELATED APPLICATIONS

This application is a U.S. National Phase filing under 35 U.S.C. 371 claiming priority to International Ser. No. PCT/US2009/064666 filed Nov. 17, 2009, which claims priority to U.S. Provisional Application 61/116,910, filed Nov. 21, 2008, each of which is incorporated herein by reference in its entirety.

The present invention relates to the use of an antisense oligonucleotide (ASO) therapeutic targeted to eukaryotic translation initiation factor 4E (eIF-4E) in combination with cisplatin in order to achieve an enhanced therapeutic effect in treating cancers.

eIF-4E is elevated in multiple human cancers and is directly related to disease progression. Elevated eIF-4E function triggers enhanced assembly of the eIF-4F translation initiation complex, which includes eIF-4E as a component, driving the expression of a pool of mRNAs that are exceptionally dependent on elevated eIF-4F activity for translation and which promote tumor cell growth, proliferation, development, survival, and angiogenesis. In view of the involvement of eIF-4E in tumor growth and development, this protein is an attractive therapeutic target.

PCT International Publication WO 2005/028628 discloses ASOs targeted to eIF-4 E, including the ASO disclosed herein, and methods of using these ASOs for modulating the expression or overexpression of eIF-4E in vitro and in vivo.

Graff et al. (2007) *J. Clin. Invest.* 117:2638-48 discloses studies on a number of ASOs targeted to eIF-4E, also including the ASO disclosed herein.

Cisplatin (cis-Diamminedichloroplatinum (II); cis-DDP; Platinol-AQ) is a platinum coordination complex used to treat carcinomas of the testis, ovary, bladder, head and neck, esophagus, lung, thyroid, cervix, and edometrium, as well as neuroblastoma and osteogenic sarcomas (Chabner et al. (2001) in *Goodman & Gilman's The Pharmacological Basis of Therapeutics*, Tenth Edition, Hardman, Limbird, and Gilman, eds., McGraw-Hill, pages 1385, and 1432-34).

There exists a need for improved therapies for the treatment of cancers. The combined use of the chemically modified eIF-4E ASO disclosed herein, which has been shown to selectively reduce gene and protein expression of eIF-4E, with cisplatin in 2 different human xenografted cancer models variously results in an additive, or greater-than-additive, effect in reducing tumor volume compared to the reduction in tumor volume achieved with the ASO or cisplatin alone. The chemical modifications of the ASO enhance resistance to degradation by cellular nucleases and increase nucleic acid duplex stability with the eIF-4E mRNA target. The high target selectivity of the ASO minimizes non-target related undesired and adverse side effects. Both cisplatin and the ASO can be administered systemically and distribute throughout the body. The combination of the ASO and cisplatin is therefore a potent and effective therapeutic combination of high selectivity in cancer cells. In addition, the drug combination disclosed herein possesses other highly desirable pharmacologic properties, such as high bioavailability associated with intravenous administration, good in vivo metabolic stability, and pharmacokinetic/pharmacodynamic properties that permit convenient dosing.

Thus, among its various aspects, the present invention provides:

A method of treating lung cancer, comprising administering to a patient in need thereof a therapeutically effective combination of cisplatin and a modified eIF-4E antisense oligonucleotide which is in the form of a pharmaceutically acceptable salt. The pharmaceutically acceptable salt can be a sodium salt. In another embodiment of this aspect of the invention, cisplatin is administered after administration of the modified eIF-4 E antisense oligonucleotide, within a therapeutically effective interval. In a further embodiment, the therapeutically effective interval is in the range of from about 4 days to about 21 days.

A method of treating lung cancer, comprising administering to a patient in need thereof a modified eIF-4E antisense oligonucleotide which is in the form of a pharmaceutically acceptable salt, and cisplatin in amounts that in combination are effective in treating said lung cancer. The pharmaceutically acceptable salt can be a sodium salt. In another embodiment of this aspect of the invention, cisplatin is administered after administration of the modified eIF-4E antisense oligonucleotide, within a therapeutically effective interval. In a further embodiment, the therapeutically effective interval is in the range of from about 4 days to about 21 days.

A method of treating lung cancer, comprising sequentially administering to a patient in need thereof an amount of a modified eIF-4E antisense oligonucleotide which is in the form of a pharmaceutically acceptable salt, followed by an amount of cisplatin, wherein said amounts of said modified eIF-4E antisense oligonucleotide and said cisplatin in combination are effective in treating said lung cancer in said patient, and wherein said cisplatin is administered within a therapeutically effective interval after administration of said modified eIF-4E antisense oligonucleotide. The pharmaceutically acceptable salt can be a sodium salt. In an embodiment of this aspect of the invention, the therapeutically effective interval is in the range of from about 4 days to about 21 days.

A method of treating non-small cell lung cancer, comprising:

administering to a patient in need thereof a cisplatin-sensitizing amount of a modified eIF-4E antisense oligonucleotide which is in the form of a pharmaceutically acceptable salt, followed by administering to said patient an effective amount of cisplatin within a therapeutically effective interval, wherein together said amounts result in an additive or greater-than-additive reduction in the volume of a non-small cell lung cancer tumor compared to the sum of the reductions in the volume of said non-small cell lung cancer tumor achieved by administering said modified eIF-4E antisense oligonucleotide alone and said cisplatin alone. The pharmaceutically acceptable salt can be a sodium salt. In an embodiment of this aspect of the invention, the therapeutically effective interval is in the range of from about 4 days to about 21 days.

A method of sensitizing a non-small cell lung cancer cell to cisplatin, comprising:

contacting said non-small cell lung cancer cell and a cisplatin-sensitizing amount of a modified eIF-4E antisense oligonucleotide which is in the form of a pharmaceutically acceptable salt, and subsequently contacting said non-small cell lung cancer cell and an effective amount of cisplatin within an effective interval. The pharmaceutically acceptable salt can be a sodium salt. In an embodiment of this aspect of the invention, the effective interval is in the range of from about 4 days to about 21 days.

A method of inhibiting the growth or proliferation of a non-small cell lung cancer cell, comprising contacting said non-small cell lung cancer cell with:
an amount of a modified eIF-4E antisense oligonucleotide which is in the form of a pharmaceutically acceptable salt, and
an amount of cisplatin,
wherein said amounts of said modified eIF-4E antisense oligonucleotide and said cisplatin are effective in combination in inhibiting the growth or proliferation of said non-small cell lung cancer cell. The pharmaceutically acceptable salt can be a sodium salt. In an embodiment of this aspect of the invention, the non-small cell lung cancer cell is first contacted with the modified eIF-4E antisense oligonucleotide, and subsequently with cisplatin, within an effective interval. In a further embodiment, the effective interval is in the range of from about 4 days to about 21 days.

A method of inhibiting the growth or proliferation of a non-small cell lung cancer cell, comprising:
contacting said non-small cell lung cancer cell and a cisplatin-sensitizing amount of a modified eIF-4E antisense oligonucleotide which is in the form of a pharmaceutically acceptable salt, followed by
contacting said non-small cell lung cancer cell and an effective amount of cisplatin within an effective interval,
wherein together said amounts produce an additive or greater-than-additive effect in inhibiting the growth or proliferation of said non-small cell lung cancer cell compared to the sum of the effect achieved with said modified eIF-4E antisense oligonucleotide alone and said cisplatin alone. The pharmaceutically acceptable salt can be a sodium salt. In an embodiment of this aspect of the invention, the effective interval is in the range of from about 4 days to about 21 days.

A method of inhibiting lung tumor growth, comprising administering to a patient in need thereof a modified eIF-4E antisense oligonucleotide which is in the form of a pharmaceutically acceptable salt, and cisplatin in amounts that in combination are effective in inhibiting growth of said lung tumor. The pharmaceutically acceptable salt can be a sodium salt. In an embodiment of this aspect of the invention, cisplatin is administered after administration of the modified eIF-4E antisense oligonucleotide, within a therapeutically effective interval. In a further embodiment, the therapeutically effective interval is in the range of from about 4 days to about 21 days.

A method of inhibiting increase in tumor volume of a non-small cell lung cancer tumor, comprising:
administering to a patient in need thereof a cisplatin-sensitizing amount of a modified eIF-4E antisense oligonucleotide which is in the form of a pharmaceutically acceptable salt, followed by
administering an effective amount of cisplatin within a therapeutically effective interval,
wherein together said amounts produce an additive or greater-than-additive reduction in inhibiting tumor volume increase of said non-small cell lung cancer tumor compared to the sum of the reductions in tumor volume increase achieved by administering said modified eIF-4E antisense oligonucleotide alone and said cisplatin alone. The pharmaceutically acceptable salt can be a sodium salt. In an embodiment of this aspect of the invention, the therapeutically effective interval is in the range of from about 4 days to about 21 days.

A method of enhancing the therapeutic effectiveness of cisplatin in treating lung cancer, comprising administering to a patient in need thereof a therapeutically effective combination of (1) a modified eIF-4E antisense oligonucleotide which is in the form of a pharmaceutically acceptable salt, and (2) cisplatin. The pharmaceutically acceptable salt can be a sodium salt. In an embodiment of this aspect of the invention, cisplatin is administered after administration of the modified eIF-4E antisense oligonucleotide, within a therapeutically effective interval. In a further embodiment, the therapeutically effective interval is in the range of from about 4 days to about 21 days.

Use of the compound of formula I:

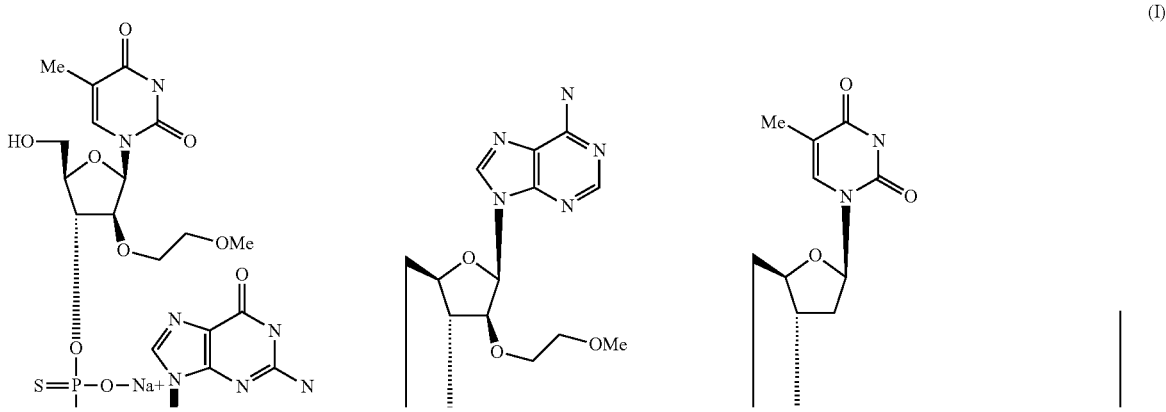

-continued
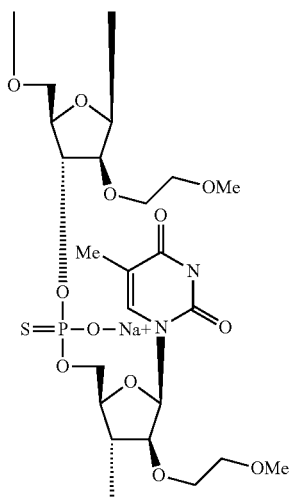
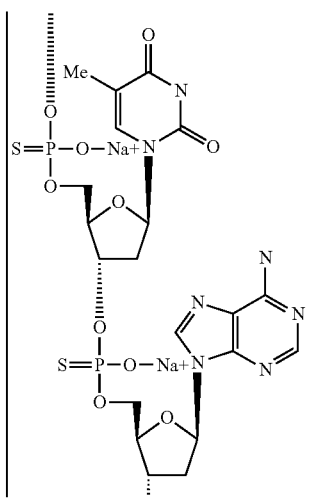
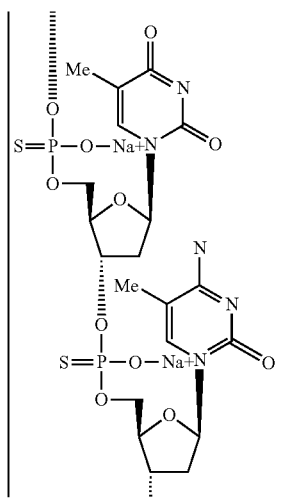
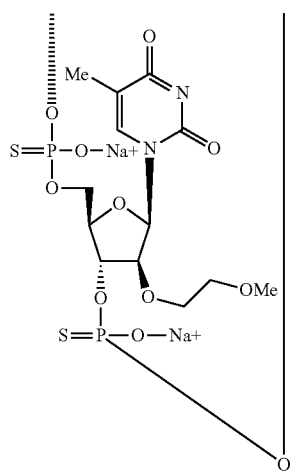
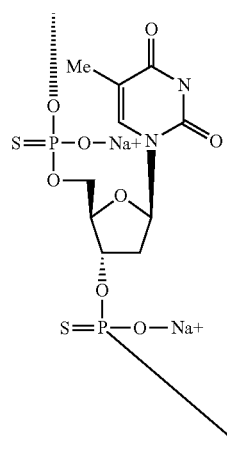
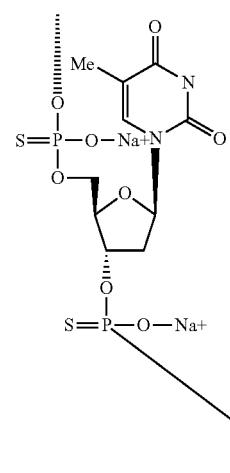
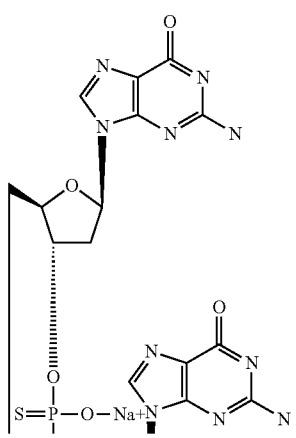
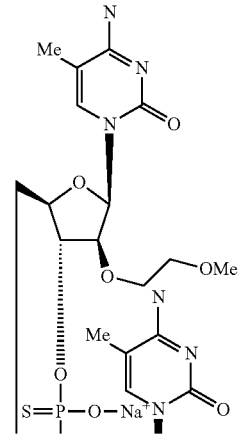

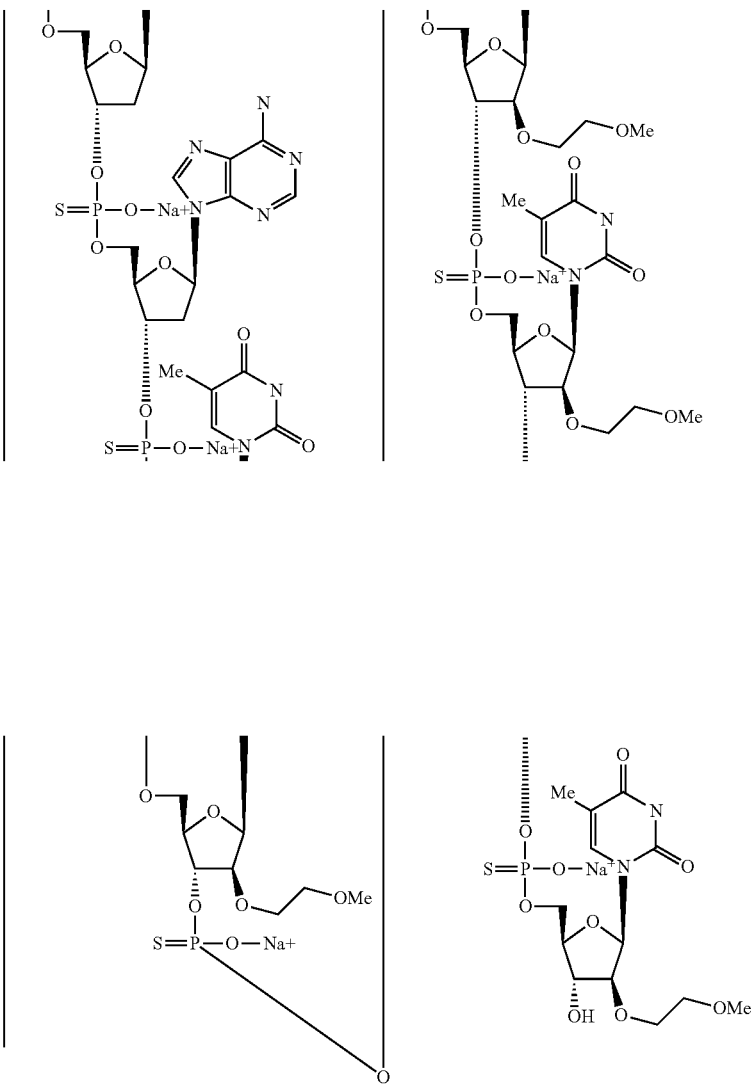

or other pharmaceutically acceptable salt thereof in the manufacture of a medicament for use in combination therapy for treating non-small cell lung cancer in a patient, wherein said medicament is to be administered in combination with cisplatin. In an embodiment of this aspect of the invention, the compound of formula I, or other pharmaceutically acceptable salt thereof, and cisplatin are administered separately, within a therapeutically effective interval. In a further embodiment, the cisplatin is administered after the compound of formula I or other pharmaceutically acceptable salt thereof, within a therapeutically effective interval. In a further embodiment, the therapeutically effective interval is in the range of from about 4 days to about 21 days. In further embodiments of any of these uses, the combination therapy is via the parenteral route, preferably via intravenous administration, more preferably via slow infusion. In a further embodiment of any of these uses, each of the compound of formula I, or other pharmaceutically acceptable salt thereof, and cisplatin is in the form of a sterile injectable solution.

A product containing the compound of formula I:
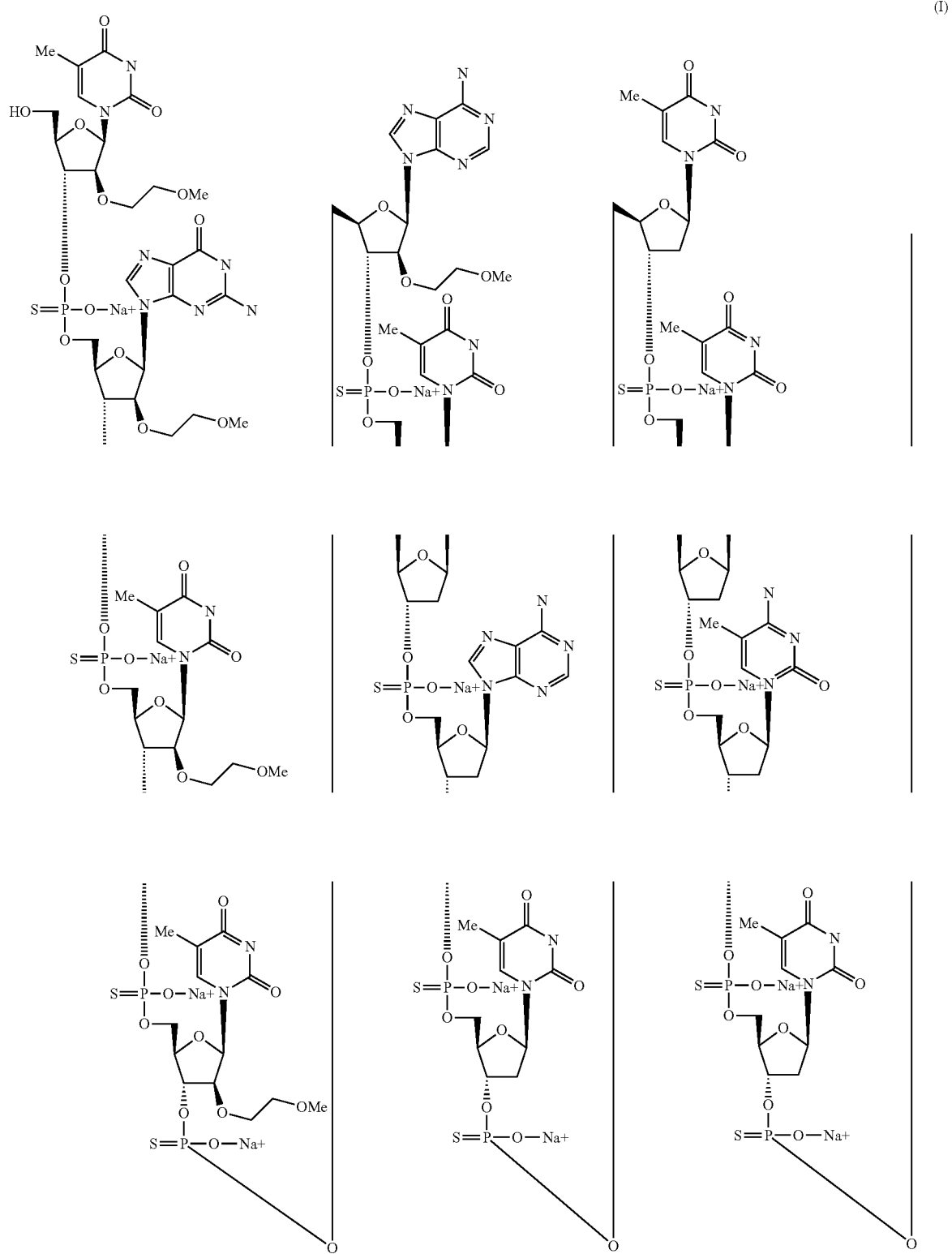
(I)

-continued

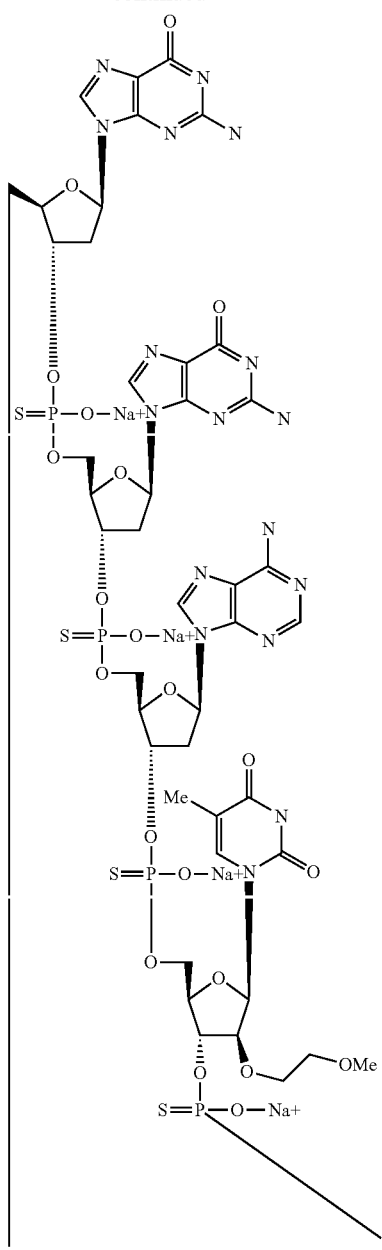

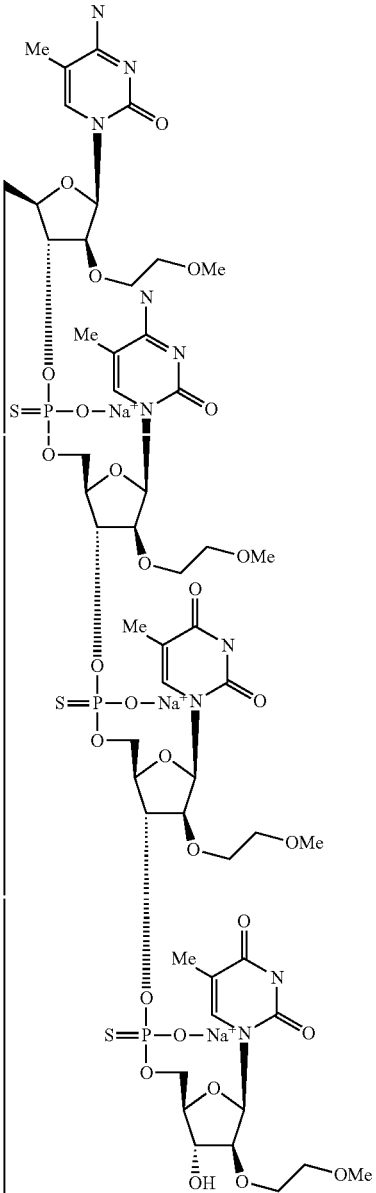

50 or other pharmaceutically acceptable salt thereof and cisplatin as a combined preparation for simultaneous or separate use in treating non-small cell lung cancer. In an embodiment of this aspect of the invention, each of the compound of formula I, or other pharmaceutically acceptable salt thereof, and cisplatin is in the form of a sterile injectable solution.

Tables 1 and 2 show the effect of combined administration of the eIF-4E ASO and cisplatin on mean tumor volume of human non-small cell lung cancer xenografts of A549 and H1975 cells, respectively, in mice. The data indicate that the combination treatment variously results in an additive (A549 xenograft) or greater-than-additive (H1975 xenograft) reduction in mean tumor volume depending upon the tumor type compared to the reductions achieved via treatment with either drug agent alone.

Combination Therapy in Cancer

Clinical protocols in cancer chemotherapy commonly employ multiple drugs rather than a single therapeutic. When each drug alone exhibits inhibitory effects, the combined effect may be antagonism, additivity, or synergism. If one of the drugs has no effect by itself but increases the effects of other drug(s), the result is called potentiation. Prediction of synergy is difficult. Each drug in combination has its own effects, i.e., its own potency and a specific shape of dose-effect curve. These effects are also related to affinity and efficacy. Factors such as feedback inhibition, spatial, temporal, and microenvironmental factors (such as pH, ionic strength, and temperature) add to the biological complexity and intricacy of drug effects. Further factors complicating prediction of synergy include individual drug absorption, permeability, transport, and metabolic activation and inactivation. Hypotheses of the possible occurrence of synergism ultimately require confirmation by experimental findings (Rideout and Chou (1991) in Chou and Rideout, Eds., *Synergism and Antagonism in Chemotherapy*, Academic Press, Inc., New York, pp. 6 and 21). Prediction of additivity is similarly difficult, and antagonism is always a possibility when multiple drugs are administered in combination.

Mizushima et al. ((1995) *Anticancer Res.* 15(1):37-43) discloses that investigators should use caution when using antisense oligonucleotides for chemosensitization of cells. Pretreatment with antisense oligonucleotides can at times have a tendency to reduce rather than enhance drug cytotoxicity. This may be caused by a number of nonspecific oligonucleotide effects, such as the ability of the oligonucleotide to interact directly with the cytotoxic drug (Blagosklonny et al. (1994) *Anticancer Drugs* 5(4):437-442).

In the case of the present drug combination, cis-platinum compounds react with nitrogen atoms of DNA, preferentially with the N-7 atom of deoxyguanylic acid. The most frequent adducts are dGpdG and dApdG, resulting from cis-platinum complex binding to adjacent deoxyguanylates or an adjacent deoxyadenylate and deoxyguanylate in a DNA strand to produce an intrastrand cross-link in both circumstances. The platinum atom can also bind to the N-7 of deoxyguanylate in one strand of DNA and to the N-7 atom of a deoxyguanylate in the complementary strand, producing an interstrand cross-link. The DNA adducts formed by platinum compounds other than cisplatin appear to be similar to those formed by cisplatin (M. Colvin (2003) in *Holland Frei Cancer Medicine* 6, D. W. Kufe et al., eds., BC Decker, Inc., Hamilton, Chapter 51, pages 768-9). The eIF-4 E ASO disclosed herein contains a gga nucleotide motif at nucleotides 13-15 reading from the 5' end, and may therefore be susceptible to the formation of such adducts with cisplatin and other platinum-containing antitumor compounds.

In view of all the foregoing factors, demonstration by the present inventor of the cisplatin-sensitizing effect of the eIF-4E ASO in cancer cells and the additive or greater-than-additive effect in inhibiting cancer cell proliferation and tumor growth achieved by the combined use of the eIF-4E ASO and cisplatin are novel, surprisingly unexpected, and therapeutically useful.

Definitions

The term "eIF-4E antisense oligonucleotide" or "eIF-4E ASO" as used herein refers to the eIF-4E antisense oligonucleotide originally described in WO 2005/028628 and known by the chemical name: d(P-thio) ([2'-O-(2-methoxyethyl)]m5rU-([2'-O-(2-methoxyethyl)]rG-([2'-O-(2-methoxyethyl)]m5rU-([2'-O-(2-methoxyethyl)]mSrC-([2'-O-(2-methoxyethyl)]rA-T-A-T-T-m5C-m5C-T-G-G-A ([2'-O-(2-methoxyethyl)]m5rU-([2'-O-(2-methoxyethyl)]m5rC-([2'-O-(2-methoxyethyl)]m5rC-([2'-O-(2-methoxyethyl)]m5rU-([2'-O-(2-methoxyethyl)]m5rU) which is in the form of a pharmaceutically acceptable salt, preferably an alkali metal salt, more preferably a lithium, sodium, or potassium salt, and most preferably a sodium salt. The chemical structure of the latter is:

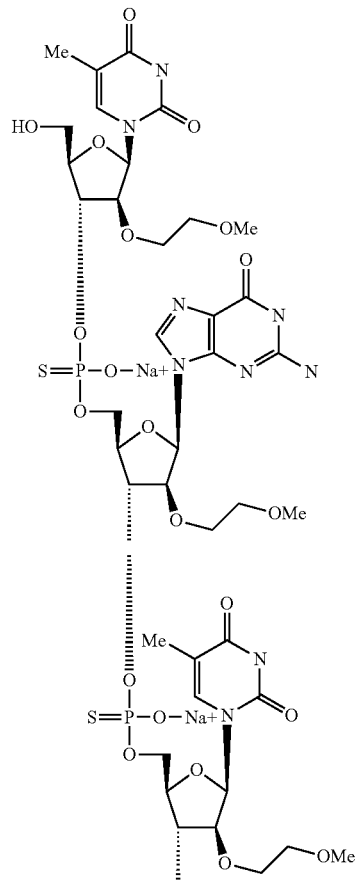
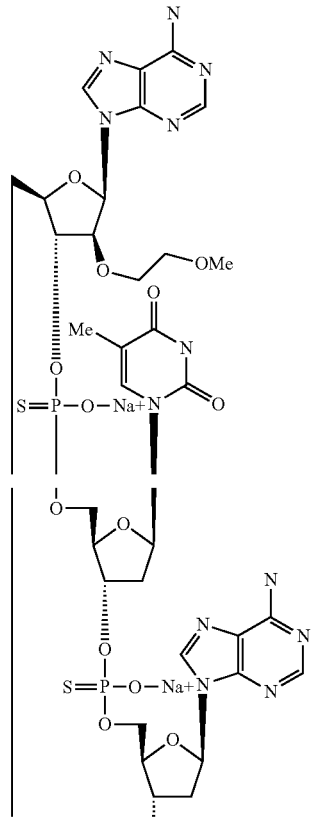
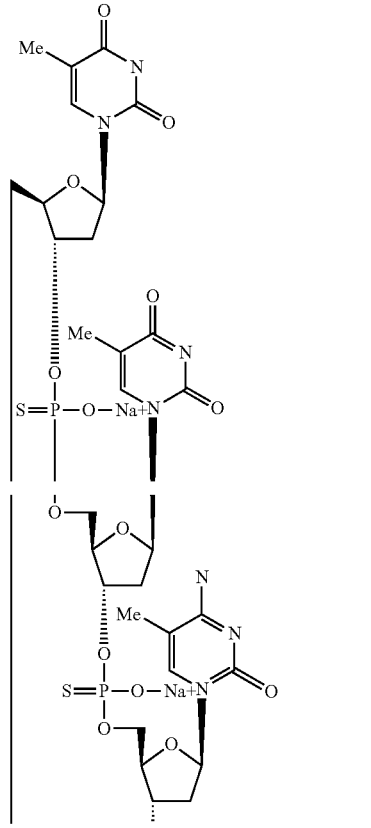

15 16
-continued
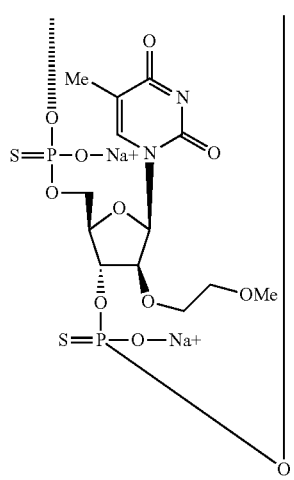
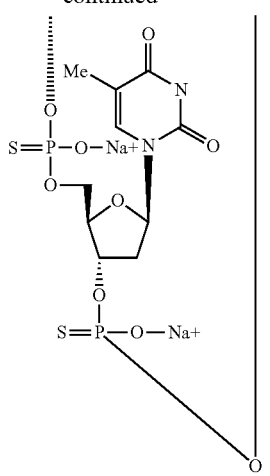
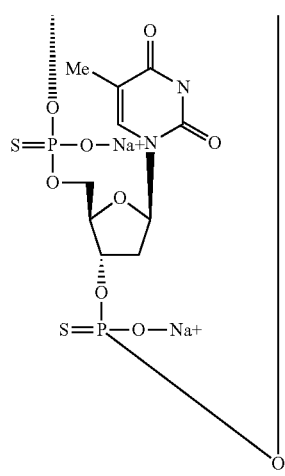
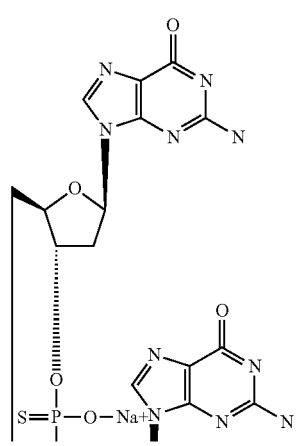
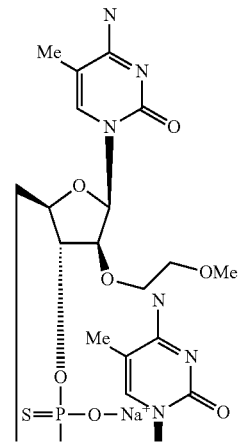
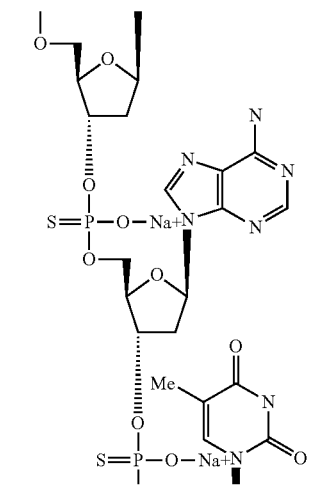
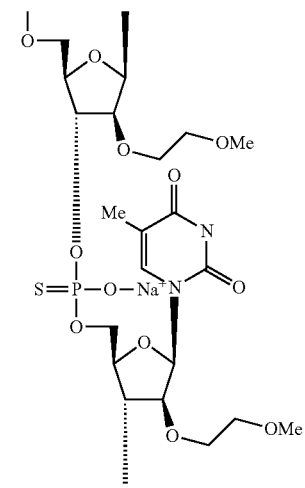

-continued

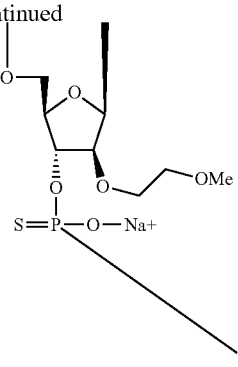
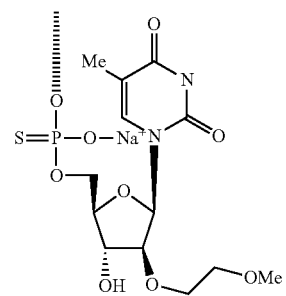

The eIF-4E ASO is described in PCT International Publication WO 2005/028628.

Cisplatin (cis-Diamminedichloroplatinum II) is an antineoplastic agent belonging to the family of platinum coordination complexes. It is a divalent inorganic water-soluble, platinum-containing complex.

The structures of cisplatin and related platinum-containing antitumor agents are:

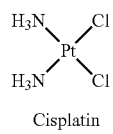

Cisplatin

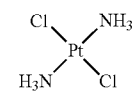

trans analogue of cisplatin

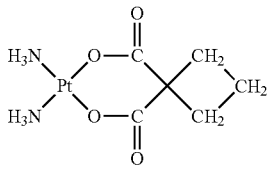

Carboplatin

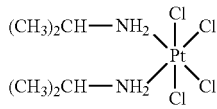

Iproplatin (CHIP)

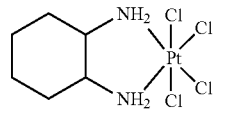

Tetraplatin (Ormaplatin)

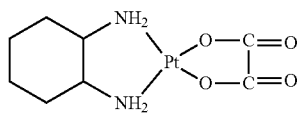

Oxaliplatin

-continued

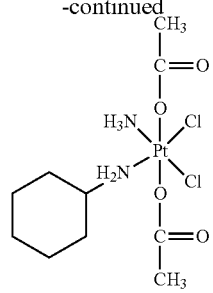

JM215

As used herein, the term "patient" refers to a mammal afflicted with one or more disorders associated with eIF-4E expression or overexpression. The most preferred patient is a human.

The term "treating" (or "treat" or "treatment") refers to curative treatment of disorders associated with eIF-4E activity, including various cancers. Curative treatment refers to processes involving a slowing, interrupting, arresting, controlling, stopping, reducing, or reversing the progression or severity of a symptom, disorder, condition, or disease, but does not necessarily involve a total elimination of all disease-related symptoms, disorders, or conditions, or the disease itself.

"Inhibiting" means restraining, retarding, restricting, reducing, holding back, or preventing.

The phrase "sensitizing to cisplatin" and the like in connection with the eIF-4E ASO means making responsive to, susceptible to the action(s) of, or readily or easily affected by, cisplatin. In some cases, this can also mean eliciting a greater response to a dose or amount of cisplatin than that which would occur in the absence of the ASO.

The term "cisplatin-sensitizing amount" refers to an amount or dose of the eIF-4E ASO that is effective in making cancer cells responsive to, susceptible to the action(s) of, or readily or easily affected by, cisplatin, or eliciting a greater cancer cell response to the action of an amount or dose of cisplatin than that which would occur in response to this amount or dose of cisplatin in the absence of the eIF-4E ASO.

Therapeutically effective amounts of the eIF-4E ASO, which include cisplatin-sensitizing amounts in the therapeutic context, are in the range of from about 100 mg to about 1,200 mg in humans. A preferred dose in terms of efficacy and tolerability is about 1,000 to about 1,200 mg per single dose or administration, administered parenterally, preferably intravenously, more preferably via slow intravenous infusion, over 1-3 hours.

"Effective amount of cisplatin" refers to an amount or dose of cisplatin, when used in combination with the eIF-4E ASO, that produces the particular cancer cell growth- or proliferation-inhibiting effect, tumor growth inhibiting effect, tumor volume increase-inhibiting effect, or cancer treatment effect in a cancer cell or tumor.

Cispatin, and carboplatin, are approved both in the United States and internationally, and are used extensively. Because the primary toxicity of carboplatin is hematopoietic, its use is preferable in patients in which non-hematopietic toxicity should be avoided. Therapeutically, Cisplatin (Platinol-AQ) is usually administered intravenously at a dose of 20 mg/m$^2$/day for 5 days, or 100 mg/m$^2$, given once every 4 weeks. Doses as high as 40 mg/m$^2$/day for 5 consecutive days have been used alone or in combination therapy for the treatment of patients with advanced ovarian cancer, but result in greater renal, hearing, and neurological toxicity. Renal toxicity can be prevented by hydrating the patient by infusing 1 to 2 liters of normal saline prior to cisplatin treatment. The appropriate amount of cisplatin is then diluted in a solution of dextrose and saline, and administered intravenously over a period of 6 to 8 hours (Chabner et al. (2001) in *Goodman & Gilman's The Pharmacological Basis of Therapeutics*, Tenth Edition, Hardman, Limbird, and Gilman, eds., McGraw-Hill, N.Y., page 1433). Cisplatin (and other platinum antitumor agents) can also be administered intravenously, either as a single dose or daily for several days, with repeat courses at 3 to 4 weeks. It is given as an infusion over several hours rather than as a bolus dose, and at very high doses, can be given as a 24 hour or longer infusion. Additional regimens and modes of administration are disclosed in M. Colvin (2003) in *Holland Frei Cancer Medicine* 6, D. W. Kufe et al., eds, BC Decker, Inc., Hamilton, Chapter 51, pages 770-771, who discloses that cispatin and carboplatin have also been administered regionally, e.g., intraperitoneally, intraarterially, intravesicularly, and into the pericardial sac. Cisplatin can also be administered intravenously at a dose of 75 mg/m$^2$ on day 1 of a 21 or 28 day schedule in combination with other agents. Doses as high as 100 mg/m$^2$ every 21 days have been used alone or in combination therapy for the treatment of patients with advanced cancer.

In general, optimum dosages of each of the present therapeutic agents can vary depending on the relative potency of the active ingredients in individual patients. Medical practitioners can determine dose and repetition rates for dosing based on measured residence times and concentrations of the active ingredients in bodily fluids or tissues and/or monitoring of relevant disease-related biomarkers for particular cancers.

In view of the additive and greater-than-additive treatment effects disclosed herein achieved via the combined use of the eIF-4E ASO and cisplatin, it is expected that subclinically effective amounts of cisplatin, compared to those when this drug is used alone, will be therapeutically effective in the methods of combination therapy disclosed herein. For any individual patient, therapeutically effective amounts of the eIF-4E ASO and cisplatin when used in combination can be determined by the healthcare provider by monitoring the effect of the combination on a relevant cancer biomarker. In the case of lung cancer, relevant biomarkers can be assessed by chest radiography, computed tomography (CT), low-dose spiral CT evaluation, magnetic resonance imaging (MRI), gallium scanning (scintigraphy), or position emission tomographic (PET) scanning. Analysis of the data obtained by these methods permits modification of the treatment regimen during therapy so that optimal amounts of the eIF-4E ASO and cisplatin in combination therapy are administered, and so that the duration of treatment can be determined as well. In this way, the dosing/treatment regimen can be modified over the course of therapy so that the lowest amounts of the eIF-4E ASO and cisplatin used in combination that exhibit satisfactory therapeutic effectiveness are administered, and so that administration of these compounds is continued only so long as is necessary to successfully treat the patient.

The term "effective interval" is a period of time beginning upon contact of a cancer cell and the eIF-4E ASO and during which the cell is responsive to the cell growth- and proliferation-inhibiting effects of the combination of the ASO and cisplatin. This effect can be manifested by: (a) sensitization of the cancer cell to the effects of cisplatin; (b) inhibition of growth or proliferation of the cancer cell; (c) inhibition of tumor growth; (d) inhibition of increase in tumor volume; or (d) therapeutically enhanced cancer treatment effect, in a cancer cell or tumor. In the case of the non-small cell lung cancer tumor xenografts disclosed herein, the effective interval is initially 8 days.

The therapeutically effective eIF-4E ASO/cisplatin combination therapies disclosed herein can be achieved by separate administration of the eIF-4E ASO and cisplatin. The ASO can be administered first, followed by administration of cisplatin within a therapeutically effective interval. When administered separately, the eIF-4E ASO and cisplatin can be introduced into the patient on different schedules, as long as the time between the two administrations falls within a therapeutically effective interval. A "therapeutically effective interval" is a period of time after administration of the eIF-4E ASO to a patient during which a tumor is responsive to the beneficial anti-neoplastic therapeutic effects of the combination of the ASO and cisplatin. For example, the initial therapeutically effective interval upon commencement of patient therapy can include a pre-cisplatin treatment period comprising administration of 3 loading doses of the eIF-4E ASO, i.e., a 1-3 hour infusion of the eIF-4E ASO once per day for 3 consecutive days during the first week, followed by administration of at least 1 weekly maintenance dose of the ASO for an additional 2 weeks. After 21 days of administration of the eIF-4E ASO in this manner, cisplatin can then be administered. Thus, the initial therapeutically effective interval can be 21 days from initiation of treatment with the eIF-4E ASO, which includes 3 loading doses during the first week followed by 2 once-weekly maintenance doses. This regimen sensitizes the tumor cells to the anti-proliferative insult delivered by cisplatin. When cisplatin is administered with the eIF-4E ASO on day 21, the patient is first given a 1-3 hour intravenous infusion of the eIF-4E ASO, followed by administration of cisplatin within 30-60 minutes after the end of the eIF-4E ASO infusion. Cisplatin is conventionally administered via a 1 hour intravenous infusion. After the initial 21 days of treatment, this regimen can be repeated every 21 days over the course of therapy, employing further maintenance doses, but without further loading doses. Thus, subsequent therapeutically effective intervals after the initial 21 day therapeutically effective interval can be 21 days after administration of eIF-4E ASO/cisplatin combinations on the same day. As in the case of the amounts of the eIF-4E ASO and cisplatin effective in the combination therapeutic methods disclosed herein, a therapeutically effective interval for any individual patient undergoing treatment with the eIF-4E ASO and cisplatin can be determined by monitoring of a biomarker appropriate for the cancer. As noted above, a variety of different biomarkers useful in monitoring non-small cell lung cancer are available for this purpose. It should be noted that the 21 day intervals discussed above in connection with both the initial therapeutically effective interval and the subsequent therapeutically effective intervals represent typical starting procedures that are flexible and subject to modification. These intervals can be further optimized, and can be shorter or longer, the effectiveness of which can be monitored via the use of relevant biomarkers as noted above.

In another embodiment, treatment with the eIF-4E ASO and cisplatin can include a pre-cisplatin treatment period comprising administration of 3 loading doses of the eIF-4 E ASO, i.e., a 1-3 hour infusion of the eIF-4E ASO once per day for 3 consecutive days during the first week, followed by administration of both the eIF-4E ASO and cisplatin as described above during the second week. Thus, the therapeutically effective interval in this case is about 4-7 days. This can be followed by administration of the eIF-4E ASO only during each of the next two succeeding weeks, followed by administration of the ASO and cisplatin again during the next week. Thus, cisplatin can be administered every approximately 21 days in conjunction with weekly administration of the eIF-4E ASO after the second week of therapy in which the eIF-4E ASO and cisplatin are both administered, for as long as treatment continues.

Thus, in view of the different treatment regimens discussed above comprising various intervals within which cisplatin can be administered after administration of the eIF-4E ASO, in particular embodiments, therapeutically effective intervals include about 4 days to about 21 days, about 4 days to about 7 days, about 14 days, and about 21 days after administration of the eIF-4E ASO alone. When the eIF-4E ASO and cisplatin are employed in the present in vivo methods, the effective interval can also be about 4 days to about 21 days, about 4 days to about 7 days, about 14 days, and about 21 days after administration of the eIF-4E ASO alone.

The eIF-4E ASO is used in the form of a pharmaceutically acceptable salt, preferably an alkali metal salt, more preferably a lithium, sodium, or potassium salt, most preferably a sodium salt. Such salts, and common methodology for preparing them, are well known in the art. See, e.g., P. Stahl et al. (2002) *Handbook of Pharmaceutical Salts: Properties, Selection and Use*, VCHA/Wiley-VCH; Berge et al. (1977) "Pharmaceutical Salts," *Journal of Pharmaceutical Sciences* 66(1):1-19. Cisplatin is a non-salt trihydrate.

The compounds of the present invention can be used as medicaments in human or veterinary medicine, administered by a variety of routes. Most preferably, such compositions are for parenteral administration, especially intravenous administration by slow infusion. Administration of solutions of these compounds, especially sterile injectable, non-pyrogenic solutions, by slow intravenous infusion is most preferred. Such pharmaceutical compositions can be prepared by methods well known in the art (See, e.g., *Remington: The Science and Practice of Pharmacy*, 19th ed. (1995), A. Gennaro et al., Mack Publishing Co.), and comprise compounds of the invention and a pharmaceutically acceptable carrier, diluent, or excipient.

The following non-limiting example illustrates the present invention.

EXAMPLE 1

Reduction of Lung Tumor Volume by Combined Use of the eIF-4E ASO and Cisplatin

To determine whether the eIF-4E ASO complements or enhances the activity of cisplatin, the effect of the combined use of the eIF-4E ASO and cisplatin on tumor volume in human xenograft cancer models is studied as follows.

Xenograft studies are carried out as described in Graff et al. (2005) *Cancer Res.* 65:7462-7469. Five million human cancer cells representing non-small cell lung cancer (line A549; ATCC, accession no. CCL-185; line NCI-H1975; ATCC, accession no. CRL-5908) are injected subcutaneously in the flank of 6-8 week old, athymic nude mice (Harlan, Indianapolis, Ind.) in a 1:1 mixture of serum-free growth medium and matrigel (Becton Dickinson, Bedford, Mass., catalogue #354234). Mice are monitored daily for palpable tumors.

When tumor volumes reach ~50-100 mm$^3$, mice are randomized to treatment groups (Graff et al. (2007) *J. Clin. Invest.* 117:2638-48). Body weight is monitored each time tumors are measured.

For treatment, all mice are injected intravenously with the eIF-4E ASO in saline in a total volume of 200 µl. The ASO consists of the nucleotide sequence 5'-TGTCATATTCCTG-GATCCTT-3' (SEQ ID NO:1), in which every internucleoside linkage is a phosphorothioate linkage, nucleotides 1-5 and 16-20 reading from the 5' end to the 3' end each comprise a 2'-O-(2-methoxyethyl) sugar, nucleotides 6-15 are 2'-deoxynucleotides, every cytosine residue is a 5-methylcytosine, and which is in the form of a sodium salt. The mice are first injected with an initial loading dose of 50 mg/kg ASO for 3 consecutive days, followed by 50 mg/kg thrice weekly thereafter.

Cisplatin dosing begins 8 days after the first ASO dose to allow time for reduction of eIF-4E protein expression. Mice are dosed intraperitoneally (IP) with 2 or 5 mg/kg cisplatin (Teva Parenteral Medicines, Inc.; 0703-5748-11) from an infusion concentrate diluted in saline, in a volume of 200 µl once weekly for 65 days. One mL of infusion concentrate (1 mg/mL) contains 1 mg cisplatin, 9 mg sodium chloride, hydrochloric acid and/or sodium hydroxide to pH 3.2-4.4, and water for injection.

The vehicle only group is dosed with saline.

All animal work is performed with Institutional Animal Care and Use Committee approval in an AALAC-certified facility.

Tumor volumes are calculated measuring the largest (L) and smallest (W) diameters with a caliper. The formula is: Volume=L×W$^2$×0.534. Tumor volume data are transformed to a log scale to equalize variance across time and treatment groups. The log volume data are analyzed with a two-way repeated measures analysis of variance by time and treatment using SAS PROC MIXED software (SAS Institute Inc, Cary, N.C.) using the spatial power covariance structure. Treatment groups are compared to the control group at each time point and overall. The data may be plotted as means and standard errors for each treatment group versus time. Additivity is assessed in two ways: (1) as an overall interaction effect between the ASO and cisplatin in the repeated measures analysis, and (2) by using the Bliss Independence method on the final day of the study (C. I. Bliss (1939) *Ann. AppL Biol.* 26:585-615). These two methods yield the same results.

The results are presented in Tables 1-4, below.

TABLE 1

A549 Xenograft Tumor Volumes in Response to Various Treatments

| A549 NSCLC Day | Vehicle Mean | SE | eIF-4E ASO Mean | SE | Cisplatin, 5 mg/kg Mean | SE | eIF-4E ASO + Cisplatin, 5 mg/kg Mean | SE | Signif. vs. Vehicle | #Mean if Additive | Significance of Interaction Effect |
|---|---|---|---|---|---|---|---|---|---|---|---|
| 11 | 83.96 | 17.87 | 86.39 | 16.76 | 85.43 | 12.98 | 85.5 | 18.32 | NS | 87.90 | 0.945 |
| 14 | 96.55 | 20.54 | 87.36 | 16.95 | 94.63 | 14.37 | 78.14 | 16.74 | NS | 85.62 | 0.821 |
| 18 | 126.88 | 27 | 141.7 | 27.49 | 124.68 | 18.94 | 118.86 | 25.46 | NS | 139.24 | 0.696 |
| 21 | 151.52 | 32.24 | 134.88 | 26.16 | 137.74 | 20.92 | 141.36 | 30.28 | NS | 122.61 | 0.725 |
| 25 | 202.74 | 43.14 | 212.4 | 41.2 | 210.75 | 32.01 | 219.87 | 47.1 | NS | 220.79 | 0.992 |
| 28 | 257.23 | 54.73 | 251.64 | 48.81 | 238.78 | 36.27 | 238.9 | 51.53 | NS | 233.59 | 0.940 |
| 32 | 309.38 | 65.83 | 309.94 | 60.12 | 283.12 | 43.01 | 244.54 | 53.15 | NS | 283.63 | 0.745 |
| 36 | 372.07 | 79.17 | 402.67 | 78.11 | 310.61 | 47.18 | 337.03 | 73.72 | NS | 336.16 | 0.978 |
| 40 | 457.58 | 97.37 | 439.54 | 85.26 | 367.44 | 55.81 | 292.23 | 64.26 | NS | 352.95 | 0.690 |
| 43 | 516.73 | 109.95 | 499.06 | 96.81 | 412.68 | 62.69 | 295.29 | 65.15 | NS | 398.57 | 0.512 |
| 47 | 562.87 | 119.77 | 455.53 | 88.36 | 405.18 | 61.55 | 288.74 | 63.94 | * | 327.91 | 0.826 |
| 50 | 627.28 | 133.47 | 463.92 | 89.99 | 428.84 | 65.14 | 279.8 | 62.12 | ** | 317.16 | 0.843 |
| 54 | 697.77 | 148.47 | 520.9 | 101.04 | 478.35 | 72.66 | 298.94 | 66.55 | ** | 357.10 | 0.748 |
| 57 | 628.35 | 133.7 | 550.29 | 106.74 | 482.77 | 73.33 | 293.46 | 65.45 | ** | 422.80 | 0.430 |
| 61 | 673.9 | 143.4 | 597.72 | 115.95 | 478.95 | 72.75 | 262.26 | 58.61 | ** | 424.81 | 0.293 |
| 64 | 681.01 | 144.91 | 618.75 | 120.02 | 529.51 | 80.43 | 279.54 | 63.04 | ** | 481.10 | 0.228 |
| 68 | 721.43 | 153.51 | 594.08 | 115.24 | 520.83 | 79.11 | 276.59 | 63.01 | ** | 428.89 | 0.353 |
| 71 | 663.26 | 141.13 | 566.2 | 109.83 | 564.57 | 85.76 | 242.74 | 55.66 | *** | 481.95 | 0.133 |
| 75 | 786.22 | 167.29 | 608.86 | 118.11 | 535.33 | 81.32 | 311.23 | 71.88 | ** | 414.57 | 0.577 |

Predicted mean if additive for the combination effect is calculated as (ASO Volume) × (cisplatin volume)/(Vehicle volume).
NS = Not Significant
* p < 0.05
** p < 0.01
*** p < 0.001

TABLE 2

Percent Reduction of A549 Tumor Size on Day 75 (negative number indicates reduction vs. control):

| Day | Vehicle | eIF-4E ASO | Cisplatin, 5 mg/kg | eIF-4E ASO + Cisplatin, 5 mg/kg | Additive Effect |
|---|---|---|---|---|---|
| 75 | 0 | −22.6% | −31.9% | −60.4% | −47.3% |

Tables 1 and 2 show that: (1) the combination of the ASO with cisplatin at 5 mg/kg significantly inhibits tumor growth in A549 xenografts after day 43 relative to the vehicle control, and (2) this combination has an observed greater than additive effect that is not statistically significantly greater than additive.

TABLE 3

H1975 Xenograft Tumor Volumes in Response to Various Treatments

| H1975 NSCLC Day | Vehicle Mean | SE | eIF-4E ASO Mean | SE | Cisplatin, 5 mg/kg Mean | SE | eIF-4E ASO + Cisplatin, 5 mg/kg Mean | SE | Signif. Vs Vehicle | #Mean if Additive | Significance of Interaction Effect |
|---|---|---|---|---|---|---|---|---|---|---|---|
| 7 | 42.91 | 8.58 | 45.83 | 8.99 | 40.02 | 4.77 | 47.99 | 11.8 | NS | 42.74 | 0.787 |
| 12 | 93.44 | 18.68 | 85.9 | 16.86 | 90.76 | 10.82 | 81.59 | 20.07 | NS | 83.44 | 0.958 |
| 15 | 150.94 | 30.18 | 121.6 | 23.86 | 112.12 | 13.36 | 105.22 | 25.88 | NS | 90.33 | 0.721 |
| 19 | 244.16 | 48.82 | 255.64 | 50.17 | 172.5 | 20.56 | 145.34 | 35.75 | NS | 180.61 | 0.612 |
| 22 | 429.58 | 85.89 | 376.84 | 73.96 | 295.95 | 35.27 | 194.08 | 47.75 | ** | 259.62 | 0.497 |
| 26 | 796.43 | 159.24 | 742.98 | 145.81 | 595.06 | 70.91 | 272.39 | 67.01 | *** | 555.12 | 0.100 |
| 29 | 1144.48 | 228.83 | 1100.19 | 215.91 | 863.18 | 102.86 | 396.04 | 97.43 | *** | 829.78 | 0.088 |
| 33 | 1761.92 | 352.28 | 1485.65 | 291.56 | 1221.36 | 145.55 | 557.43 | 137.13 | *** | 1029.85 | 0.155 |

TABLE 3-continued

H1975 Xenograft Tumor Volumes in Response to Various Treatments

| H1975 NSCLC Day | Vehicle Mean | Vehicle SE | eIF-4E ASO Mean | eIF-4E ASO SE | Cisplatin, 5 mg/kg Mean | Cisplatin, 5 mg/kg SE | eIF-4E ASO + Cisplatin, 5 mg/kg Mean | eIF-4E ASO + Cisplatin, 5 mg/kg SE | eIF-4E ASO + Cisplatin, 5 mg/kg Signif. Vs Vehicle | #Mean if Additive | Significance of Interaction Effect |
|---|---|---|---|---|---|---|---|---|---|---|---|
| 36 | 2188.33 | 437.53 | 2164.31 | 424.75 | 1740.85 | 207.45 | 720.42 | 177.23 | *** | 1721.74 | 0.045 |
| 40 | 2781.68 | 556.17 | 2901.75 | 569.47 | 2095.44 | 249.71 | 925.28 | 227.62 | *** | 2185.89 | 0.048 |
| 43 | 3480.1 | 695.81 | 3881.36 | 761.72 | 2798.22 | 333.46 | 1271.42 | 312.78 | *** | 3120.86 | 0.039 |

Predicted mean if additive for the combination effect is calculated as (ASO Volume) × (cisplatin volume)/(Vehicle volume).
NS = Not Significant
* p < 0.05
** p < 0.01
*** p < 0.001

TABLE 4

Percent Reduction of H1975 Tumor Size on Day 43 (negative number indicates reduction vs. control)

| Day | Vehicle | ASO | Cisplatin, 5 mg/kg | ASO + Cisplatin, 5 mg/kg | Additive Effect |
|---|---|---|---|---|---|
| 43 | 0 | 11.5% | −19.6% | −63.5% | −10.4% |

Tables 3 and 4 show that: (1) the combination of the ASO with cisplatin at 5 mg/kg significantly inhibits tumor growth in H1975 xenografts after day 19 relative to the vehicle control, and (2) this combination has a greater than additive effect that is statistically significant after day 33.

In both cases, treatment with the eIF-4E ASO sensitizes the tumor cells to the cell growth- and proliferation-inhibiting action of cisplatin. In each case, the tumor volume of the combination therapy group is less than that of the cisplatin therapy group. These results demonstrate at least an additive effect when the ASO and cisplatin are used in combination in these lung cancer xenograft models compared to either drug alone.

What is claimed is:

1. A method of treating lung cancer, comprising administering to a patient in need thereof a therapeutically effective combination of cisplatin and a modified eIF-4E antisense oligonucleotide which is in the form of a pharmaceutically acceptable salt, wherein said cisplatin is administered after administration of said modified eIF-4E antisense oligonucleotide, within a therapeutically effective interval.

2. The method of claim 1, wherein said therapeutically effective interval is in the range of from about 4 days to about 21 days.

3. The method of claim 2, wherein the modified eIF-4E antisense oligonucleotide is a compound of formula I:

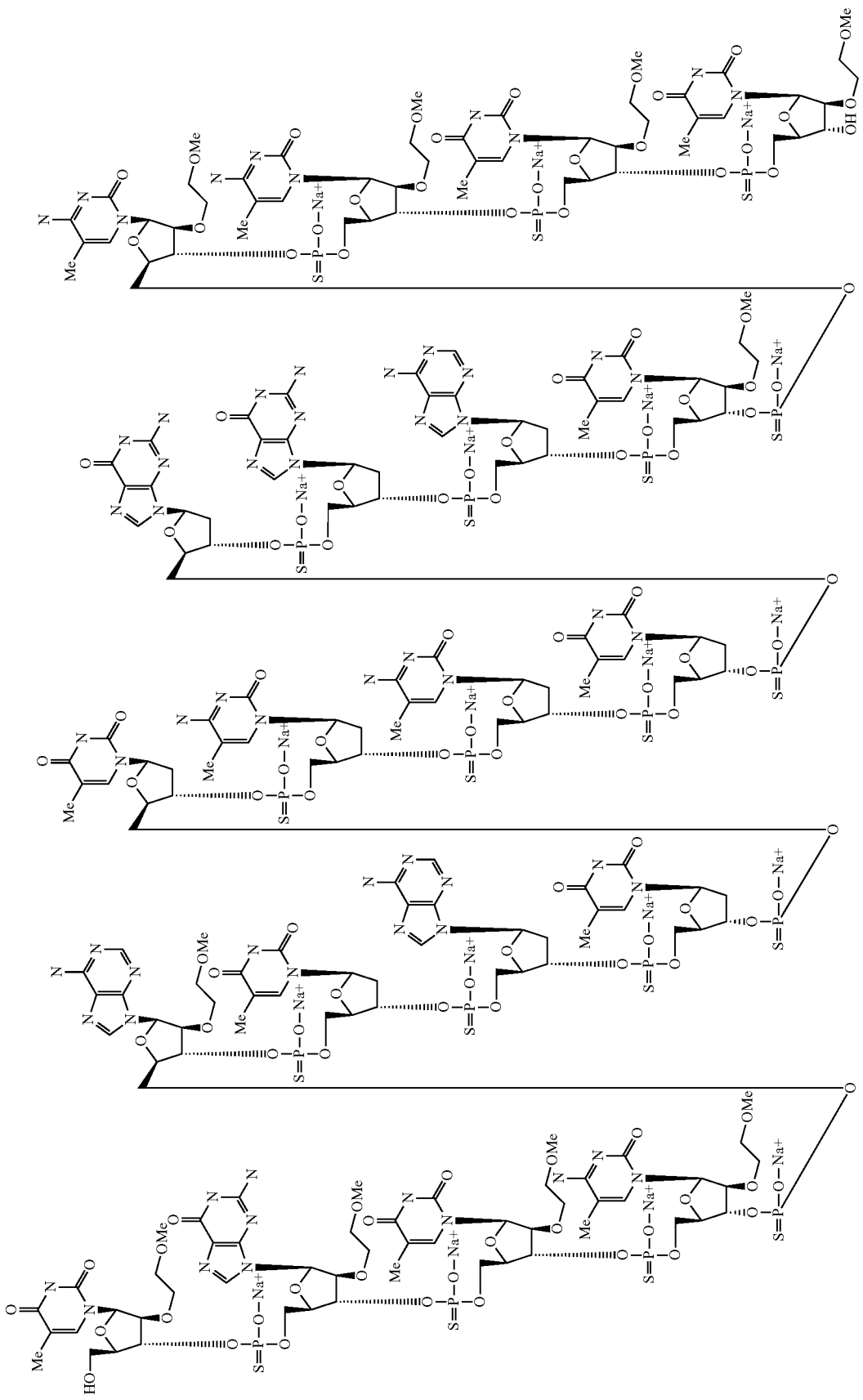

or other pharmaceutically acceptable salt thereof.

4. The method of claim 3, wherein said combination is administered via the parenteral route.

5. The method of claim 3, wherein said combination is administered intravenously.

6. The method of claim 5, wherein said intravenous administration is via slow infusion.

7. A method of treating lung cancer, comprising administering to a patient in need thereof a modified eIF-4E antisense oligonucleotide which is in the form of a pharmaceutically acceptable salt, and cisplatin in amounts that in combination are effective in treating said lung cancer, wherein said cisplatin is administered after administration of said modified eIF-4E antisense oligonucleotide, within a therapeutically effective interval.

8. The method of claim 7, wherein said therapeutically effective interval is in the range of from about 4 days to about 21 days.

9. The method of claim 8, wherein the modified eIF-4E antisense oligonucleotide is a compound of formula I:

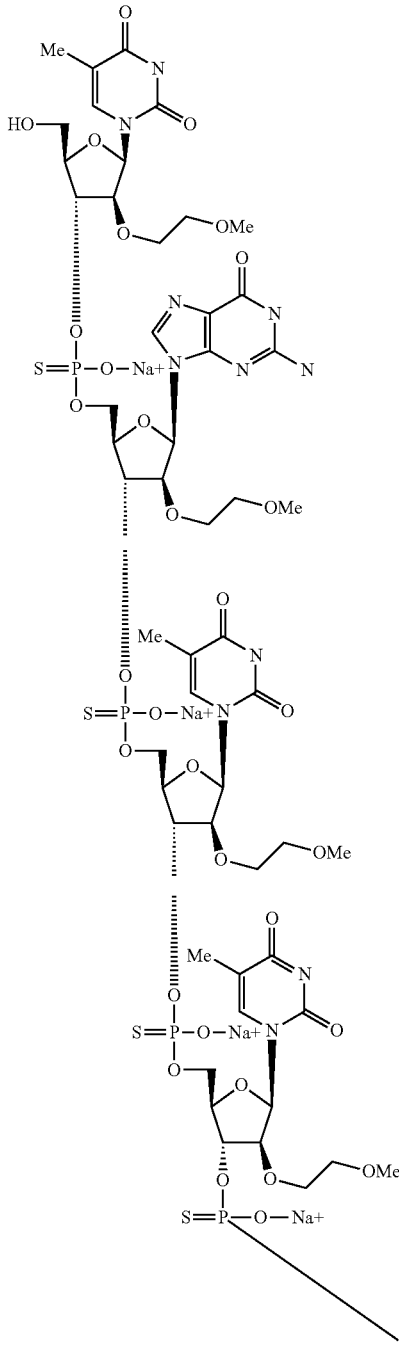
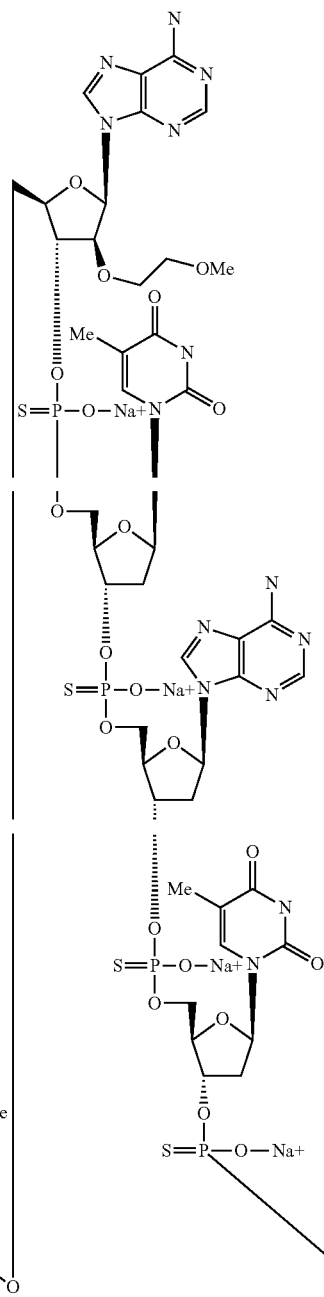
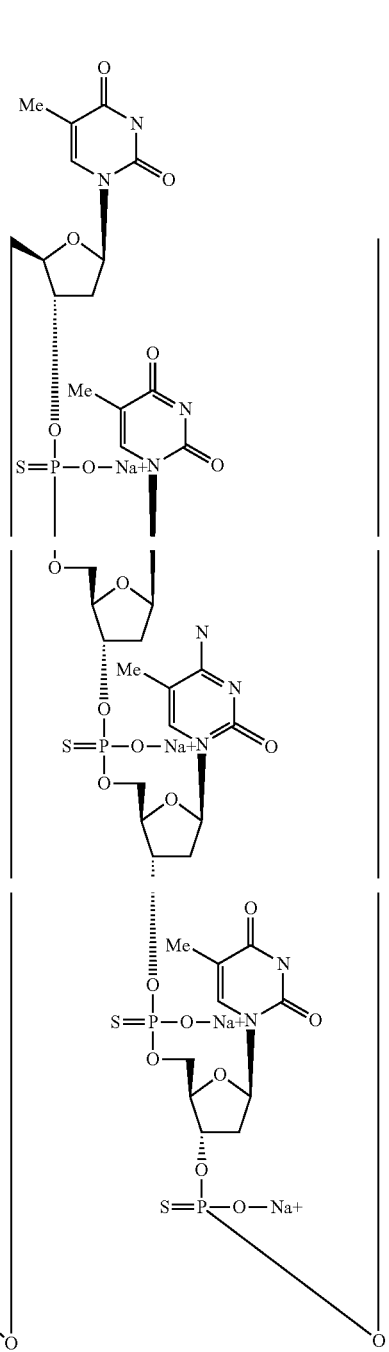

(I)

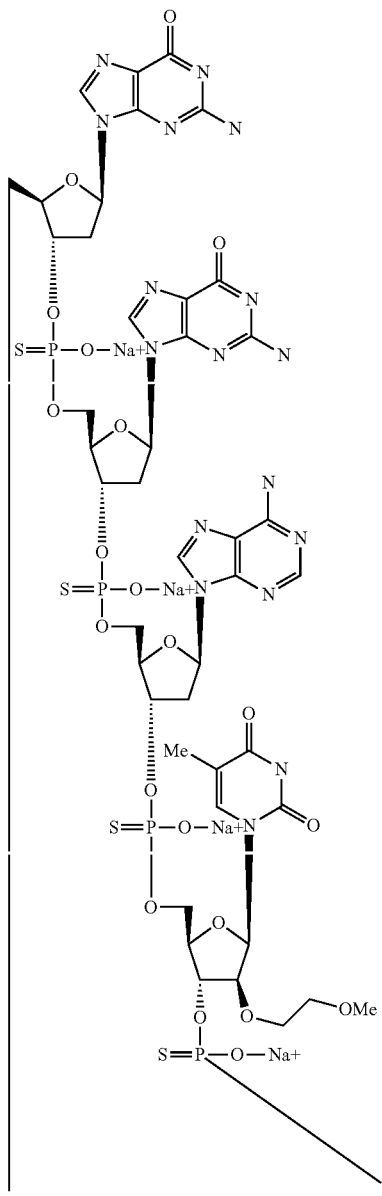
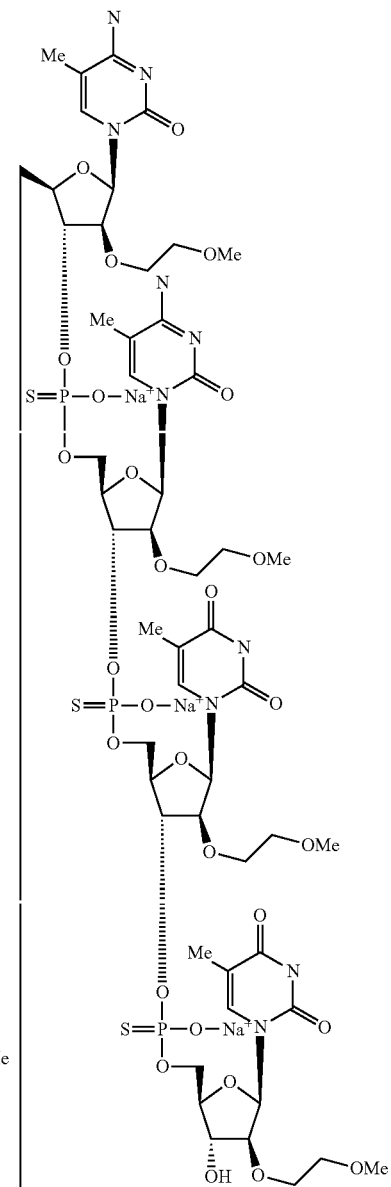

or other pharmaceutically acceptable salt thereof.

10. The method of claim 7, wherein said modified eIF-4E antisense oligonucleotide and cisplatin are administered via the parenteral route.

11. The method of claim 7, wherein said modified eIF-4E antisense oligonucleotide and cisplatin are administered intravenously.

12. The method of claim 11, wherein said intravenous administration is via slow infusion.

* * * * *